United States Patent
Averback et al.

(12) 
(10) Patent No.: US 6,461,608 B1
(45) Date of Patent: Oct. 8, 2002

(54) BACTERIOPHAGE COMPOSITION USEFUL IN TREATING FOOD PRODUCTS TO PREVENT BACTERIAL CONTAMINATION

(75) Inventors: Paul Averback, Beaconsfield; Jack Gemmell, Mississauga, both of (CA)

(73) Assignee: Nymox Pharmaceutical Corporation, St. Laurent (CA)

( * ) Notice: Subject to any disclaimer, the term of this patent is extended or adjusted under 35 U.S.C. 154(b) by 8 days.

(21) Appl. No.: 09/718,093

(22) Filed: Nov. 22, 2000

(51) Int. Cl.$^7$ .............................................. A01N 63/00

(52) U.S. Cl. .................... 424/93.6; 435/235.1; 435/239

(58) Field of Search ............................. 435/235.1, 239; 424/93.6, 543, 404

(56) References Cited

U.S. PATENT DOCUMENTS 6,121,036 A * 9/2000 Ghanbari et al. ........ 435/235.1
6,322,783 B1 * 11/2001 Takahashi .................. 424/93.6

OTHER PUBLICATIONS

Abstract of Monod et al., "The genome of the pseudo T–even bacteriophages, a diverge group that Resembles T4", *Journal of Molecular Biology 267/2*, pp. 8–9, ©Elsevier Science B.V. (1997).
abstract of Mosig et al., "A novel mechanism of virus–virus interactions: Bacteriophage P2 tin protein inhibits phage T4 DNA synthesis by poisioning the T4 single–stranded DNA binding protein, gp32", *Virology 230/1*, pp. 3–4, ©Elsevier Science B.V., (1997).
Abstract of Jonosi et al., "Molecular cloning and expression of a novel hydroxymenthylcytosine–specific restriction enzyme (PvuRts 110) modulated by glucosylation of DNA", *J. Mol. Biol 242/1*, pp. 5 and 7, ©Elsevier Science B.V., (1994).
Abstract of Shapiro et al., "Predicting RNA H–type pseudoknots with the massively parallel genetic algorithm", *Comput. Appl. Biosci, 13/4*, p. 2, ©Elsevier Science B.V., (1997).
Abstract of Cummings et al., "Structural aberrations in T even bacteriophage. IX Effect of mixed infected on the production of giant bacteriophage", *J. Virol. (Balt) 22/2*, p. 14, ©Elsevier Science, B.V., (1977).
Abstract of Bayer et al., Structural aberrations in T even bacteriophage. VIII. Surface morphology of T4 lollipops, *Virology, 76/2*, p. 15, ©Elsevier Science B.V., (1977).
Abstract of Aebi et al., Capsid fine structure of T even bacteriophages. Binding and localization of two dispensable capsid proteins into the P23 surface lattice, *J. Molec. Biol. 110/4*, p. 16, ©Elsevier Science B.V., (1977).
Abstract of Russell R., "Comparative genetics of the T even bacteriophages", *Genetics 78/4*, p. 17, (1974).

Abstract of Taormina et al., "Comparison of Chemical treatments to eliminate enterohemorrhagic *Escherichia coli* O157:H7 on alfalfa seeds", *J Food Prot. 62 (4)*, p. 228, (Apr. 1999).
*Public Health Report 113:105*, "FDA Approves Meat Irradiation for Pathogen Control", News and Notes; Government Issues, p. 24, (Mar./Apr. 1998).
Article, "Beef Irradiation Approved, But Future Uncertain", ©Softline Information, Inc., p. 49, (Jan. 31, 1998).
Abstract of Mercola, "Current Health News You Can Use", ©Softline Information, Inc., pp. 51, 56–57, (Jan. 31, 1998).
Abstract of Klausner, "Food Irradiation: We May be Zapping Up the Wrong Tree", ©Softline Information, Inc., pp. 138–140, (Dec. 31, 1994).
"Medical Experts Urge Radiation of Beef to Kill Deadly Bacteria", © The New York Times Company, pp. 142 and 142, (Jul. 14, 1994).
Abstract of Deliganis, "Death by Apple Juice: The Problem of Foodborne Illness, the Regulatory Response, and Further Suggestions for Reform", pp. 143–205, ©The Food and Drug Law Institute, (1998).
Abstract of Mead et al., "*Escherichia coli* O157:H7", pp. 2–15, ©The Lancet Ltd., (Oct. 10, 1998).
Abstract of Perepanova et al., "The efficacy of bacteriophage preparations in treating inflammatory urologic diseases", *Urol Nefrol (Mosk) 5:14–7*, pp. 17, (Sep./Oct. 1995).
Abstract of Possehl, "The Long Reach of Bugs Without Borders", *Hospitals & Health Networks 72(13)*: pp. 19–23, (Jul. 5, 1998).
Abstract of Mackenzie, "When *E. coli* turns deadly; includes related article on *E. coli* 0157:H7; *Escherichia coli*" ©Information Access Company, pp. 28–33, (Jul. 1, 1999).
Abstract of Lake, "*E. coli* in Cattle", ©Softline Information, Inc., pp. 26–27, (Feb. 28, 2000).
Abstract of Cerrato,. "When food is the culprit; food poisioning", pp. 34–38, (Jun. 1, 1999).
Abstract of Sheff, "*Escherichia coli E. coli* 0157.H7.", ©Information Access Company, pp. 39–40, (May 1, 1999).
Abstract of Freeman, "Antimicrobial resistance: implications for clinician", ©Information Access Company, pp. 65–79, (Nov. 1997).
Abstract: "Growing menace: antibiotic–resistant 'supergerms'", ©Softline Information, Inc., pp. 41 and 42, (Fall 1998).
Abstract of Hilan et al, "Antimicrobial Effect of Essential Oil of Salvia libanotica (Sage)", ©Softline Information, Inc., pp. 58–64, Winter 1997).
Abstract of Dymsza, "Biotechnology and Food Safety", ©Softline Information, Inc., pp. 46–47, (Sep. 30, 1998).
Abstract of Greenberg et al., "Irradiated Food", ©Softline Information, Inc., pp. 102–121, (Apr. 30, 1996).

(List continued on next page.)

*Primary Examiner*—Jeffrey Stucker
(74) *Attorney, Agent, or Firm*—Foley & Lardner

(57) ABSTRACT

The present invention is directed to novel bacteriophage compositions useful in treating food products to prevent bacterial contamination.

33 Claims, 11 Drawing Sheets

OTHER PUBLICATIONS

Abstract of Buchanan et al., "Contamination of intact apples after immersion in an aqueous environment containing *Escherichia coli* 0157H7", *J. Food Prot. 62(5)*, p. 227, (May 1999).

Abstract of MacGregor et al., "Light inactivation of food–related pathogenic bacteria using a pulsed power source", *Letters in Applied Microbiology 27/2*, ©Elsevier Science B.V., p. 223, (1998).

Abstract of Ryser et al., "New food–borne pathogens of public health significance", *J. Am, Diet Assoc. 89/7*, ©Elsevier Science B.V., p. 219, (1989).

Abstract of Takata et al., "The effects of various antibacterial agents on the release of verotixin against *Escherichia coli* 0–157:H7 strains", *Japanese Journal of Chemotherapy 45/5*, ©Elsevier Science B.V., pp. 217 and 218, (1997).

Abstract of Buzby et al., "Economic costs and trade impacts of microbial foodborne illness", *World Health Statistics Quarterly 50/1–2*, ©Elsevier Science B.V., p. 215, (1997).

Abstract: "Roadside cider may be risky: may be contaminated with *E. coli*", p. 206, ©Environmental Nutrition Inc., (Sep. 1993).

Abstract: "Ban the 0157:H7 Bomb", ©Softline Information, Inc., p. 136, (Jan./Feb. 1995).

Abstract of Cooter, "*E coli* Myths", ©Softline Information, Inc., pp. 133–135, (Apr. 1995).

Abstract of Pilot et al., Threats from the food we eat; includes related articles; New and Emerging Pathogens, part 3, ©Information Access Company, pp. 122–132, (Apr. 1996).

Abstract of Koutkia et al., Enterohemorragic *Escherichia coli* 0157:H7—an emerging pathogen; includes patient information, ©Information Access Company, pp. 85–93, (Sep. 1, 1997).

\* cited by examiner

FIG. 1

TABLE 1. OPEN READING FRAMES IN Φ119u THAT HAVE HOMOLOGY TO OTHER KNOWN PHAGE PROTEINS. ORFs ARE LISTED IN THE ORDER THAT THEY APPEAR ON THE LINEAR PHAGE GENOME. THE ORFs ARE NAMED BY THE NUMBER OF AMINO ACIDS IN THE TRANSLATED SEQUENCE. ALL HOMOLOGIES ARE AT THE AMINO ACID LEVEL.

| ORF | PUTATIVE FUNCTION | DEGREE OF HOMOLOGY |
|---|---|---|
| 110 | ANTIRESTRICTION | 46% IDENTITY<br>66% SIMILARITY TO PHAGE T7 0.3 GENE. |
| 875 | RNA POLYMERASE | 85% IDENTITY<br>91% SIMILARITY TO PHAGE 5p6 RNA POLYMERASE. |
| 42 | UNKNOWN | 50% IDENTITY<br>67% SIMILARITY TO THE T7 GENE 1.1. |
| 857 | DNA POLYMERASE | ONE REGION HAS 50% IDENTITY TO T7 DNA POLYMERASE. ANOTHER REGION IS 50% IDENTICAL TO T3 POLYMERASE. |
| 173 | UNKNOWN | CONTAINS A REGION OF 45 a.a. THAT ARE 75 % IDENTICAL TO T7 GENE 1.7. |
| 516 | HEAD TO TAIL JOINING PROTEIN | ABOUT 40% IDENTICAL TO THE T3 PROTEIN. |
| 810 | TAIL TUBE PROTEIN | 45% IDENTITY IN THE N-TERMINAL REGION TO THE T7 PROTEIN. |
| 1061 | INTERNAL VIRION PROTEIN | SMALL REGION IN THE C-TERMINUS OF 30% IDENTITY TO THE T7 PROTEIN. |
| 633 | DNA MATURASE | 45% IDENTITY WITH THE T7 MATURASE. |
| 652 | K5 LYASE | 95% IDENTITY<br>96% SIMILARITY TO THE PHAGE K5 LYASE. |
| 811 | N-ACETYLNEURAMINIDASE | 97% IDENTITY<br>96% SIMILARITY TO THE PHAGE K1E NEURAMINIDASE. |

FIG. 2

B1 Head DNA Sequence

TTTCTGTAGCCAGAATACCGCTCAGTTCAGCATCAGCATCCATACCGTGTACTGGCACGGAGGTC
TTGTGCTAATTCGATAGAGTAAGCAGCTTTCAGCTGGGCGAGATTTAGCTTCGATAACTTGTTTAT
CGATACGGAAGCCCCATTTCATTCCCATGGTTATCGGTTGAACCGTTGAAACCTTCCTGGAGTT
CAGCGATAGAAGTAGCCATACCTTCAGCGATTTCTACCAGTGCACCAGCTTCCATTTGTTTCTTA
ACTTCTGCATCTAATTAGCTGCATCAGTTGCACCAGAATCAAGTGTTACGACAGCAGAAGCTTG
CAGATATACAGTACCAGTTTCTTGGAAGAAGTGAGTATAGATATCACCTACAmCAGTAGTAGTGT
CAGCAGCCAGAGCTGGGAATTTCTTAGCCAGCAGCACCCTGACCAGAGAACATCGCGTCTGGGCATAC
ATCGGATGGAAAGCTTCTTTAGCGCGTGTTCATAGGCTGAACACCACAAATATCAAAAGCGATCAGATTAG
AATACCCTGACCGGTCGGGCGTGTTCATAGGCTGAACACCACAAATATCAAAAGCGATCAGATTAG
GAATGCACGCCGC

FIG. 3

B1 Tail DNA Sequence

Created: Friday, December 18, 1998 11:50 AM

TTTCTGTAGCCAGAATACCGCTCAGTTCAGCATCAGCATCCATACCGTGTACTGCACGGAGGTCTTGTGCTA
ATTCGATAGAGTAAGCAGCTTTCAGCTGGCGAGATTTAGCTTCGATAACTTGTTTATCGATACGGAAGCCA
TTTCATTCCATGGGTTATCGGTAGAACCGTTGAAACCTTCCTGGAGTTCAGCGATAGAAGTAGCCATACCTT
CAGCGATTTCTACCAGTGCACCAGCTTCCATTGTTTCTTAACTTCTGCATCTAATTTAGCTGCATCAGTTG
CACCAGAATCAAGTGTTACGACAGAAGCTTGCAGATATACAGTACCAGTTTCTTGGAAGAAGTGAGTAT
AGATATCACCTACAmCAGTAGTGTCAGCAGCCAGAGCTGGGAATTTCTTAGCGCCAGCACCCTGACCAGAGA
ACATCGCGTCTGGGCATACATCGGATGGAAAGCTTCTTTAGCGCCAGCGATAGGGTCTTTACCATATA
CTGCACGGAGAGCAAATACCCTGACCGGTCGGGCTGTTCATAGGCTGAACACCACAAATATCAAAAGCGATCA
GATTAGGAATGCACGCCGC

FIG. 4

B1 TAIL AMINO ACID SEQUENCE

TRANSLATE DNA SEQUENCE bltailrev1.seq(1,595)
WITH STANDARD GENETIC CODE

```
MOLECULAR WEIGHT 20921.67 DALTONS
198  AMINO ACIDS
14   STRONGLY BASIC(+) AMINO ACIDS (K,R)
26   STRONGLY ACIDIC(-) AMINO ACIDS (D,E)
80   HYDROPHOBIC AMINO ACIDS (A,I,L,F,W,V)
43   POLAR AMINO ACIDS (N,C,Q,S,T,Y)

TOTAL NUMBER OF BASES TRANSLATED IS 594
% A= 25.76              [153]
% G= 23.74              [141]
% T= 27.44              [163]
% C= 22.90              [136]
% AMBIGUOUS = 0.17      [1]

% A+T = 53.20           [316]
% C+G = 46.63           [277]
```

CODON USAGE:

| | | | | | | | | | | | |
|---|---|---|---|---|---|---|---|---|---|---|---|
| gca | Ala(A) | 7 | # | cag | Gln(Q) | 5 | # | uug | Leu(L) | 0 | # | uaa | Ter(.) | 0 |
| gcc | Ala(A) | 1 | # | --- | Gln(Q) | 10 | # | --- | Leu(L) | 13 | # | uag | Ter(.) | 0 |
| gcg | Ala(A) | 3 | # | gaa | Glu(E) | 13 | # | aaa | Lys(K) | 8 | # | uga | Ter(.) | 0 |
| gcu | Ala(A) | 24 | # | gag | Glu(E) | 0 | # | aag | Lys(K) | 2 | # | --- | Ter(.) | 0 |
| --- | Ala(A) | 35 | # | --- | Glu(E) | 13 | # | --- | Lys(K) | 10 | # | aca | Thr(T) | 2 |
| aga | Arg(R) | 0 | # | gga | Gly(G) | 0 | # | aug | Met(M) | 7 | # | acc | Thr(T) | 2 |
| agg | Arg(R) | 0 | # | ggc | Gly(G) | 2 | # | --- | Met(M) | 7 | # | acg | Thr(T) | 0 |
| cga | Arg(R) | 0 | # | ggg | Gly(G) | 0 | # | uuc | Phe(F) | 7 | # | acu | Thr(T) | 8 |
| cgc | Arg(R) | 1 | # | ggu | Gly(G) | 14 | # | uuu | Phe(F) | 2 | # | --- | Thr(T) | 12 |
| cgg | Arg(R) | 0 | # | --- | Gly(G) | 16 | # | --- | Phe(F) | 9 | # | ugg | Trp(W) | 1 |
| cgu | Arg(R) | 3 | # | cac | His(H) | 2 | # | cca | Pro(P) | 3 | # | --- | Trp(W) | 1 |
| --- | Arg(R) | 4 | # | cau | His(H) | 1 | # | ccc | Pro(P) | 0 | # | uac | Tyr(Y) | 1 |
| aac | Asn(N) | 3 | # | --- | His(H) | 3 | # | ccg | Pro(P) | 2 | # | uau | Tyr(Y) | 4 |
| aau | Asn(N) | 2 | # | aua | Ile(I) | 0 | # | ccu | Pro(P) | 3 | # | --- | Tyr(Y) | 5 |
| --- | Asn(N) | 5 | # | auc | Ile(I) | 8 | # | --- | Pro(P) | 8 | # | gua | Val(V) | 7 |
| gac | Asp(D) | 4 | # | auu | Ile(I) | 3 | # | agc | Ser(S) | 2 | # | guc | Val(V) | 1 |
| gau | Asp(D) | 9 | # | --- | Ile(I) | 11 | # | agu | Ser(S) | 0 | # | gug | Val(V) | 0 |
| --- | Asp(D) | 13 | # | cua | Leu(L) | 0 | # | uca | Ser(S) | 0 | # | guu | Val(V) | 3 |
| ugc | Cys(C) | 1 | # | cuc | Leu(L) | 3 | # | ucc | Ser(S) | 0 | # | --- | Val(V) | 11 |
| ugu | Cys(C) | 1 | # | cug | Leu(L) | 7 | # | ucg | Ser(S) | 0 | # | nnn | ???(X) | 1 |
| --- | Cys(C) | 2 | # | cuu | Leu(L) | 1 | # | ucu | Ser(S) | 7 | # | TOTAL | | 198 |
| caa | Gln(Q) | 5 | # | uua | Leu(L) | 2 | # | --- | Ser(S) | 9 | # | | | |

AACIPNLIAFDICGVQPMNSPTGQVFALRAVYGKDPIAAGAKEAFHPMYAPDAMFSGQGAAKKFPALAADTTTXVGDIYT
HFFQETGTVYLQASAVVTLDSGATDAAKLDAEVKKQMEAGALVEIAEGMATSIAELQEGFNGSTDNPWNEMGFRIDKQVI
EAKSRQ_KAAYSIELAQDLRAVHGMDADAELSGILATE

FIG. 5

B3 Head DNA Sequence

```
TACCACCCTGACGGAGTAGTTATCCAATCAACAACTTCGCGGTTGATTTCCAGCATAATTTCGGTA
GCCAGAATACCAGAGACAGTTCAGCATCCATACCGTGAACAGCGCGAAGGTCTTGTGCTAA
TTCAATAGAGTAAGCAGCTTTACGCTGACGAGATTTAGCTTCGATAACTTGCTTATCGATACGGA
AGCCCATTTCATTCCATGGGTTATCGGTAGAACCGTTAAAACCTTCCTGAAGTTCAGCGATAGAA
GTAGCCATACCTTCAGCGATTCTACCAGTACACCAGCTTCCATTGTTTCTTAATTTCAGCATC
TAATTTGTCTGCGTCAGATGCGCCTGAATCAATTTGTTAACTTCTGTAGCTTGCAGATATACTG
TACCAGTTTCCTGGAAGAAGTGAGTGTAAATAGTTCCGACTTCAAAGAGTATCACTTGCTTTCAA
AGCAGCGAATTTCTTAGCAGCACCCCTGACCAGAGAACATTGCATCTGACCTTACATTGGGTGGA
ATGCTTCTTTAGCACCGGAAGCGGATTGGGTCTTTACCATATACTGCGCGCAGTGCGAATACCTGG
CCAGTCGGGCTGTGTTCATTGGCTGAACACCACAAATATCGAAGCAATCAGTAGGAATAGCACGCC
G
```

FIG. 6

B3 Tail DNA Sequence

Created: Friday, December 18, 1998 10:18 AM

```
TACCACCTGACGGAGTAGTTATCCAATCAACAACTTCGCGGTTGATTTCCAGCATAATTTCGGTAGCCAGAA
TACCAGACAGTTCAGCATCAGCATCCATACCGTGAACAGCCGAAGGTCTTGTGCTAATTCAATAGAGTAAG
CAGCTTTCAGCTGACGAGATTAGCTTCGATAACTTGCTTATCGGAAGCCCATTTCATTCCATGGT
TATCGGTAGAACCGTTAAAACCTTCCTGAAGTTCAGCATCTAATTTGTCTGCGATAGAAGTAGCCATACCTTCAGCGATTTCTACCA
GTACCAGCTTCCATTGTTTCTTGTTGCAGATATACTGTACCAGTTTCCTGGAAGAAGTGAGTGTAAATAGTTCCGACTT
GTTAACTTCTGTAGCTTGCTTTCAAAGCAGCGAATTTCTTAGCAGCACCCGATTGGTCTCTTTACCATATCGCCGCAGTCTGGAC
CAAGAGTATCACTTGCTTCTTTAGCACCGGAAGCGATTGGTCTCTTTACCACCAAATATCGAAGCAATCAGGTAGGAATAGCACGC
CATACATTGGGTGGAATGCTTCTTTAGCACCGGAAGCGATTGGTCTCTTACCATATCGAAGCAATCAGGTAGGAATAGCACGC
ATACCTGGCCAGTCGGGCTGTTCATTGGCTGAACACCACAAATATCGAAGCAATCAGGTAGGAATAGCACGC
CG
```

FIG. 7

B3 TAIL AMINO ACID SEQUENCE

TRANSLATE DNA SEQUENCE b3tailrev1.seq(2,650)
WITH STANDARD GENETIC CODE

MOLECULAR WEIGHT 23230.30 DALTONS
    216 AMINO ACIDS
    17 STRONGLY BASIC(+) AMINO ACIDS (K,R)
    32 STRONGLY ACIDIC(-) AMINO ACIDS (D,E)
    81 HYDROPHOBIC AMINO ACIDS (A,I,L,F,W,V)
    47 POLAR AMINO ACIDS (N,C,Q,S,T,Y)

TOTAL NUMBER OF BASES TRANSLATED IS 648
    % A= 27.78    [180]
    % G= 23.61    [153]
    % T= 27.47    [178]
    % C= 21.14    [137]
    % AMBIGUOUS = 0.00    [0]

% A+T = 55.25    [358]
    % C+G = 44.75    [290]

CODON USAGE:

| Codon | AA | # | Codon | AA | # | Codon | AA | # | Codon | AA | # |
|---|---|---|---|---|---|---|---|---|---|---|---|
| gca | Ala(A) | 8 | cag | Gln(Q) | 6 | uug | Leu(L) | 1 | uaa | Ter(.) | 0 |
| gcc | Ala(A) | 0 | --- | Gln(Q) | 11 | --- | Leu(L) | 15 | uag | Ter(.) | 0 |
| gcg | Ala(A) | 0 | gaa | Glu(E) | 17 | aaa | Lys(K) | 9 | uga | Ter(.) | 0 |
| gcu | Ala(A) | 19 | gag | Glu(E) | 0 | aag | Lys(K) | 3 | --- | Ter(.) | 0 |
| --- | Ala(A) | 27 | --- | Glu(E) | 17 | --- | Lys(K) | 12 | aca | Thr(T) | 2 |
| aga | Arg(R) | 0 | gga | Gly(G) | 1 | aug | Met(M) | 8 | acc | Thr(T) | 2 |
| agg | Arg(R) | 0 | ggc | Gly(G) | 4 | --- | Met(M) | 8 | acg | Thr(T) | 0 |
| cga | Arg(R) | 0 | ggg | Gly(G) | 0 | uuc | Phe(F) | 9 | acu | Thr(T) | 8 |
| cgc | Arg(R) | 3 | ggu | Gly(G) | 15 | uuu | Phe(F) | 1 | --- | Thr(T) | 12 |
| cgg | Arg(R) | 0 | --- | Gly(G) | 20 | --- | Phe(F) | 10 | ugg | Trp(W) | 2 |
| cgu | Arg(R) | 2 | cac | His(H) | 3 | cca | Pro(P) | 5 | --- | Trp(W) | 2 |
| --- | Arg(R) | 5 | cau | His(H) | 0 | ccc | Pro(P) | 0 | uac | Tyr(Y) | 2 |
| aac | Asn(N) | 4 | --- | His(H) | 3 | ccg | Pro(P) | 2 | uau | Tyr(Y) | 3 |
| aau | Asn(N) | 1 | aua | Ile(I) | 1 | ccu | Pro(P) | 1 | --- | Tyr(Y) | 5 |
| --- | Asn(N) | 5 | auc | Ile(I) | 6 | --- | Pro(P) | 8 | gua | Val(V) | 5 |
| gac | Asp(D) | 4 | auu | Ile(I) | 7 | agc | Ser(S) | 1 | guc | Val(V) | 1 |
| gau | Asp(D) | 11 | --- | Ile(I) | 14 | agu | Ser(S) | 1 | gug | Val(V) | 1 |
| --- | Asp(D) | 15 | cua | Leu(L) | 2 | uca | Ser(S) | 2 | guu | Val(V) | 6 |
| ugc | Cys(C) | . | cuc | Leu(L) | 0 | ucc | Ser(S) | 1 | --- | Val(V) | 13 |
| ugu | Cys(C) | . | cug | Leu(L) | 7 | ucg | Ser(S) | 0 | nnn | ???(X) | 0 |
| --- | Cys(C) | 2 | cuu | Leu(L) | 3 | ucu | Ser(S) | 7 | TOTAL | | 216 |
| caa | Gln(Q) | 5 | uua | Leu(L) | 2 | --- | Ser(S) | 12 | | | |

---

GVLFLPDCFDICGVQPMNSPTGQVFALRAVYGKDPIASGAKEAFHPMYGPDAMFSGQGAAKKFAALKASDTL
EVGTIYTHFFQETGTVYLQATEVKQIDSGASDADKLDAEIKKQMEAGVLVEIAEGMATSIAELQEGFNGSTD
NPWNEMGFRIDKQVIEAKSRQLKAAYSIELAQDLRAVHGMDADAELSGILATEIMLEINREVVDWITTPSGG

FIG. 8

Host range of phages B3, B1, 119u and 146a against
161 Urinary Tract Infection *E. coli* Isolates and Against *E. coli* Strain K12

| Isolate | ΦB1 | ΦB3 | Φ146a | Φ119u |
|---|---|---|---|---|
| 101 | +(p) | +(p) | + | + |
| 102 | + | +(p) | + | - |
| 103 | + | + | - | + |
| 104 | +(t) | - | +(t) | + |
| 105 | - | + | +(t) | + |
| 106 | - | - | - | - |
| 107 | +(t) | +(t) | + | - |
| 108 | + | +(t) | +(t) | - |
| 109 | + | - | - | - |
| 110 | - | +(t) | +(t) | - |
| 111 | - | + | +(t) | - |
| 112 | - | - | - | - |
| 113 | - | + | +(t) | - |
| 114 | + | +(p) | - | - |
| 115 | - | - | - | + |
| 116 | - | - | - | - |
| 117 | - | - | - | - |
| 118 | +(t) | - | - | - |
| 119 | + | - | - | + |
| 120 | +(t) | +(p) | - | + |
| 121 | +(t) | - | - | + |
| 122 | - | - | - | - |
| 123 | + | +(p) | + | - |
| 124 | - | + | - | - |
| 125 | + | - | - | - |
| 126 | + | + | - | + |
| 127 | - | + | - | - |
| 128 | - | - | + | + |
| 129 | - | +(t) | - | +(t) |
| 130 | - | - | - | - |
| 131 | + | +(t) | - | +(t) |
| 132 | + | +(t) | +(t) | - |
| 133 | +(t) | +(t) | - | - |
| 134 | - | - | - | + |
| 135 | - | + | - | - |
| 136 | + | - | - | - |
| 137 | +(t) | +(t) | - | - |
| 138 | - | - | + | + |
| 139 | + | - | - | - |
| 140 | + | + | - | +(t) |
| 141 | + | +(t) | - | - |
| 142 | - | +(t) | - | - |
| 143 | +(t) | - | - | - |
| 144 | + | +(t) | - | - |
| 145 | +(t) | + | +(t) | +(t) |
| 146 | +(t) | - | - | + |
| 147 | + | - | - | - |
| 148 | + | - | - | - |
| 149 | + | +(t) | - | - |
| 150 | - | + | +(t) | - |
| 151 | - | - | - | - |
| 152 | - | - | - | - |
| 153 | - | - | - | - |
| 154 | - | - | + | - |
| 155 | - | - | - | - |
| 156 | +(t) | - | - | - |
| 157 | - | - | - | + |
| 158 | +(t) | - | - | - |
| 159 | +(t) | - | +(t) | - |
| 160 | + | - | +(t) | - |
| 161 | + | - | + | - |
| K12 | + | + | - | - |

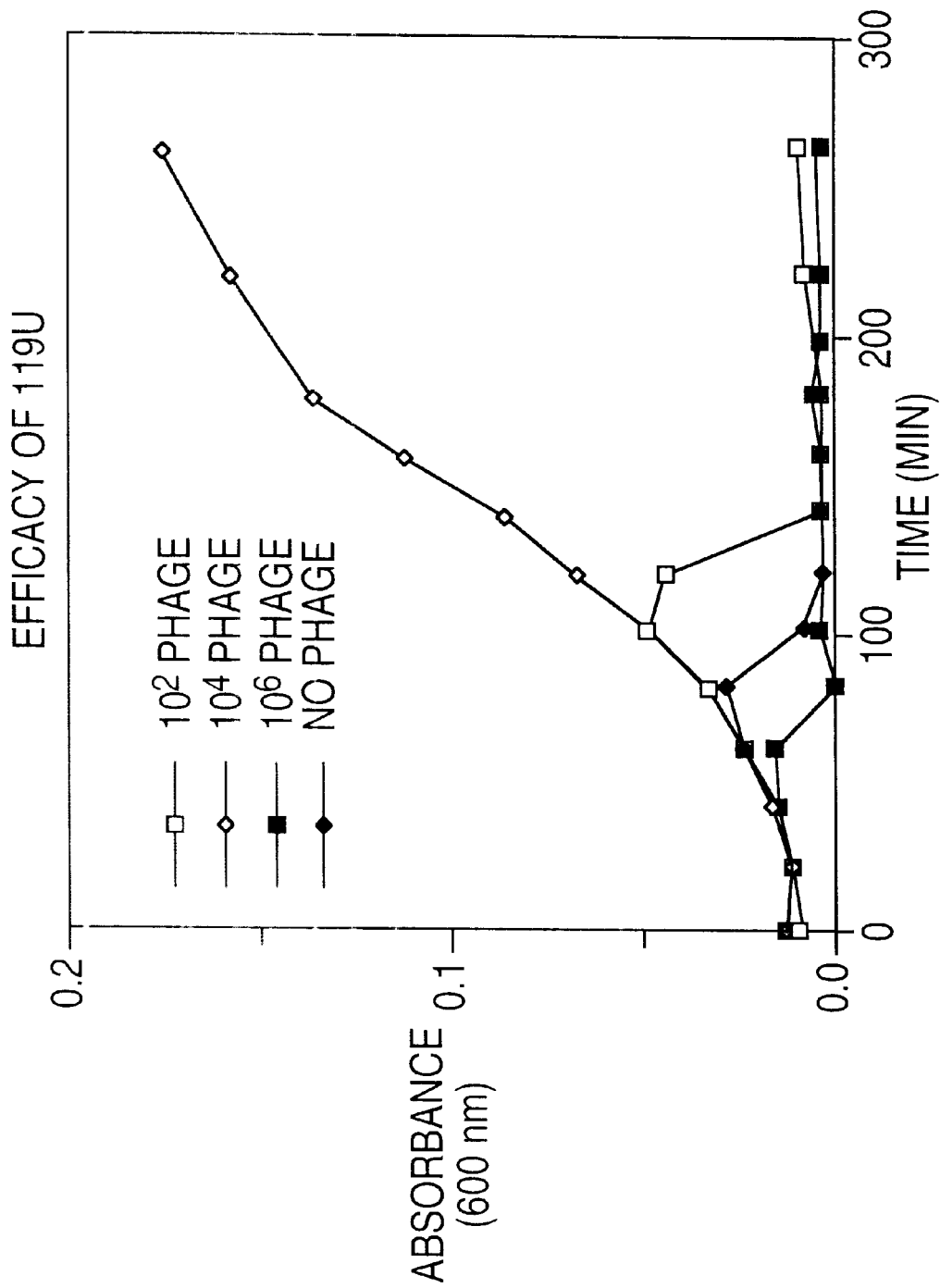

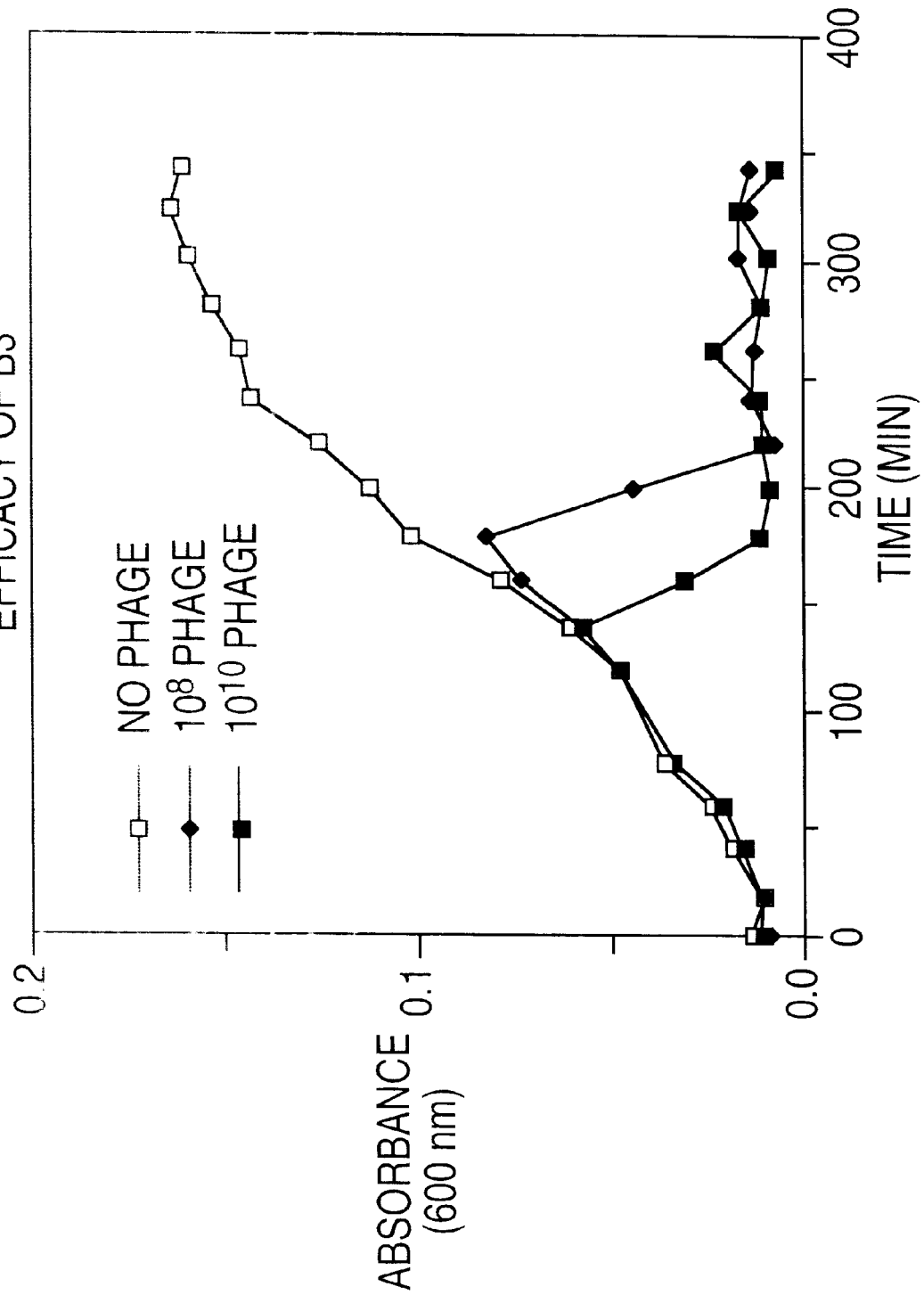

FIG. 11

Host Range of Phages B1 and B3 Against Various
Human and Porcine *E. coli* Bacterial Strains

| *E. coli* Strain | Serotype | Phage B1 | Phage B3 |
|---|---|---|---|
| 1. STJ620 | O157-VT | + | + |
| 2. STJ852 | O157-VT | + | + |
| 3. STJ788 | O157-VT | + | + |
| 4. STJ619 | O157-VT | + | + |
| 5. STJ789 | O157-VT | + | + |
| 6. STJ1160 | O157-VT | - | + |
| 7. STJ919 | O157-VT | + | + |
| 8. STJ854 | O157-VT | + | + |
| 9. STJ622 | O157-VT | + | + |
| 10. STJ787 | O157-VT | + | + |
| 11. H19 | O26-VT | + | + |
| 12. H95-106 | O1-VT | + | + |
| 13. H94-805 | O5-VT-EAE | + | + |
| 14. H85-748 | O38-VT | - | - |
| 15. H86-530 | O16-VT-EAE | + | + |
| 16. H89-39 | O45-VT-EAE | + | - |
| 17. H86-5075 | O26-VT-EAE | + | + |
| 18. H85-1158 | O85-VT-EAE | - | - |
| 19. P96-1988 | O157-STB-LT-F4 | +/- | +/- |
| 20. P96-4724 | O157-STB-LT-F4 | +/- | +/- |
| 21. P96-968A1 | O157-STB-LT-F4 | + | +/- |
| 22. P96-6098A1 | O157-STB-LT-F4 | + | + |
| 23. P99-1510(176)2B | O157 | + | + |
| 24. P99-609(176)27A | O157 | + | + |
| 25. P99-333(176)7A | O157 | + | + |
| 26. P99-6305(176)3D | O157 | + | + |
| 27. P99-6521(176)16C | O157 | + | +/- |
| 28. P97-5596(175) | O139:K82-VT2-F107 | - | +/- |
| 29. P95-00046 | O139:K82-VT2 | - | - |
| 30. P95-1884 | O138:K81-VT2-F107 | - | - |
| 31. P96-9655 | NT-VT2 | - | +/- |
| 32. P95-526 | NS-VT2 | + | + |
| 33. P95-6558 | O8:K25-VT2 | - | - |

SEQUENCE LISTING

<160> NUMBER OF SEQ ID NOS: 6

<210> SEQ ID NO 1
<211> LENGTH: 598
<212> TYPE: DNA
<213> ORGANISM: Unknown Organism
<220> FEATURE:
<223> OTHER INFORMATION: Description of Unknown Organism: Head of Phage
      B1 DNA sequence

<400> SEQUENCE: 1

| | | | | | | |
|---|---|---|---|---|---|---|
| tttctgtagc | cagaataccg | ctcagttcag | catcagcatc | cataccgtgt | actggcacgg | 60 |
| aggtcttgtg | ctaattcgat | agagtaagca | gctttcagct | ggcgagattt | agcttcgata | 120 |
| acttgtttat | cgatacggaa | gccccatttc | attcccatgg | gttatcggta | gaaccgttga | 180 |
| aaccttcctg | gagttcagcg | atagaagtag | ccataccttc | agcgatttct | accagtgcac | 240 |
| cagcttccat | ttgtttctta | acttctgcat | ctaatttagc | tgcatcagtt | gcaccagaat | 300 |
| caagtgttac | gacagcagaa | gcttgcagat | atacagtacc | agtttcttgg | aagaagtgag | 360 |
| tatagatatc | acctacamca | gtagtagtgt | cagcagccag | agctgggaat | ttcttagcag | 420 |
| caccctgacc | agagaacatc | gcgtctgggg | catacatcgg | atggaaagct | tctttagcgc | 480 |
| cagcagcgat | agggtcttta | ccatatactg | cacggagagc | aaatacctga | ccggtcgggc | 540 |
| tgttcatagg | ctgaacacca | caaatatcaa | aagcgatcag | attaggaatg | cacgccgc | 598 |

<210> SEQ ID NO 2
<211> LENGTH: 595
<212> TYPE: DNA
<213> ORGANISM: Unknown Organism
<220> FEATURE:
<223> OTHER INFORMATION: Description of Unknown Organism: Tail of Phage
      B1 DNA sequence

<400> SEQUENCE: 2

| | | | | | | |
|---|---|---|---|---|---|---|
| tttctgtagc | cagaataccg | ctcagttcag | catcagcatc | cataccgtgt | actgcacgga | 60 |
| ggtcttgtgc | taattcgata | gagtaagcag | ctttcagctg | gcgagattta | gcttcgataa | 120 |
| cttgtttatc | gatacggaag | cccatttcat | tccatgggtt | atcggtagaa | ccgttgaaac | 180 |
| cttcctggag | ttcagcgata | gaagtagcca | taccttcagc | gatttctacc | agtgcaccag | 240 |
| cttccatttg | tttcttaact | tctgcatcta | atttagctgc | atcagttgca | ccagaatcaa | 300 |
| gtgttacgac | agcagaagct | tgcagatata | cagtaccagt | ttcttggaag | aagtgagtat | 360 |
| agatatcacc | tacamcagta | gtagtgtcag | cagccagagc | tgggaatttc | ttagcagcac | 420 |
| cctgaccaga | gaacatcgcg | tctggggcat | acatcggatg | gaaagcttct | ttagcgccag | 480 |
| cagcgatagg | gtctttacca | tatactgcac | ggagagcaaa | tacctgaccg | gtcgggctgt | 540 | tcataggctg aacaccacaa atatcaaaag cgatcagatt aggaatgcac gccgc        595

<210> SEQ ID NO 3
<211> LENGTH: 198
<212> TYPE: PRT
<213> ORGANISM: Unknown Organism
<220> FEATURE:
<223> OTHER INFORMATION: Description of Unknown Organism: Tail of Phage
      B1 amino acid sequence
<220> FEATURE:
<221> NAME/KEY: MOD_RES
<222> LOCATION: (74)
<223> OTHER INFORMATION: Any amino acid

<400> SEQUENCE: 3

Ala Ala Cys Ile Pro Asn Leu Ile Ala Phe Asp Ile Cys Gly Val Gln
  1               5                  10                  15

Pro Met Asn Ser Pro Thr Gly Gln Val Phe Ala Leu Arg Ala Val Tyr
             20                  25                  30

Gly Lys Asp Pro Ile Ala Ala Gly Ala Lys Glu Ala Phe His Pro Met
         35                  40                  45

Tyr Ala Pro Asp Ala Met Phe Ser Gly Gln Gly Ala Ala Lys Lys Phe
     50                  55                  60

Pro Ala Leu Ala Ala Asp Thr Thr Thr Xaa Val Gly Asp Ile Tyr Thr
 65                  70                  75                  80

His Phe Phe Gln Glu Thr Gly Thr Val Tyr Leu Gln Ala Ser Ala Val
                 85                  90                  95

Val Thr Leu Asp Ser Gly Ala Thr Asp Ala Ala Lys Leu Asp Ala Glu
            100                 105                 110

Val Lys Lys Gln Met Glu Ala Gly Ala Leu Val Glu Ile Ala Glu Gly
        115                 120                 125

Met Ala Thr Ser Ile Ala Glu Leu Gln Glu Gly Phe Asn Gly Ser Thr
130                 135                 140

Asp Asn Pro Trp Asn Glu Met Gly Phe Arg Ile Asp Lys Gln Val Ile
145                 150                 155                 160

Glu Ala Lys Ser Arg Gln Leu Lys Ala Ala Tyr Ser Ile Glu Leu Ala
                165                 170                 175

Gln Asp Leu Arg Ala Val His Gly Met Asp Ala Asp Ala Glu Leu Ser
            180                 185                 190

Gly Ile Leu Ala Thr Glu
        195

<210> SEQ ID NO 4
<211> LENGTH: 651
<212> TYPE: DNA
<213> ORGANISM: Unknown Organism
<220> FEATURE:
<223> OTHER INFORMATION: Description of Unknown Organism: Head of Phage
      B3 DNA sequence

<400> SEQUENCE: 4
taccacctga cggagtagtt atccaatcaa caacttcgcg gttgatttcc agcataattt        60
cggtagccag aataccagac agttcagcat cagcatccat accgtgaaca gcgcgaaggt       120
cttgtgctaa ttcaatagag taagcagctt tacgctgacg agatttagct tcgataactt       180
gcttatcgat acggaagccc atttcattcc atgggttatc ggtagaaccg ttaaaacctt       240
cctgaagttc agcgatagaa gtagccatac cttcagcgat ttctaccagt acaccagctt       300
ccatttgttt cttaatttca gcatctaatt tgtctgcgtc agatgcgcct gaatcaattt       360

-continued

```
gtttaacttc tgtagcttgc agatatactg taccagtttc tggaagaag tgagtgtaaa      420 tagttccgac ttcaaagagt atcacttgct ttcaaagcag cgaatttctt agcagcaccc      480
tgaccagaga acattgcatc tggaccttac attgggtgga atgcttcttt agcaccggaa      540
gcgattgggt ctttaccata tactgcgcgc agtgcgaata cctggccagt cgggctgttc      600
attggctgaa caccacaaat atcgaagcaa tcaggtagga atagcacgcc g               651
```

<210> SEQ ID NO 5
<211> LENGTH: 650
<212> TYPE: DNA
<213> ORGANISM: Unknown Organism
<220> FEATURE:
<223> OTHER INFORMATION: Description of Unknown Organism: Tail of Phage
    B3 DNA sequence

<400> SEQUENCE: 5

```
taccacctga cggagtagtt atccaatcaa caacttcgcg gttgatttcc agcataattt      60
cggtagccag aataccagac agttcagcat cagcatccat accgtgaaca gcgcgaaggt      120
cttgtgctaa ttcaatagag taagcagctt tcagctgacg agatttagct tcgataactt      180
gcttatcgat acggaagccc atttcattcc atgggttatc ggtagaaccg ttaaaacctt      240
cctgaagttc agcgatagaa gtagccatac cttcagcgat ttctaccagt acaccagctt      300
ccatttgttt cttaatttca gcatctaatt tgtctgcgtc agatgcgcct gaatcaattt      360
gtttaacttc tgtagcttgc agatatactg taccagtttc tggaagaag tgagtgtaaa      420 tagttccgac ttcaagagta tcacttgctt tcaaagcagc gaatttctta gcagcaccct      480
gaccagagaa cattgcatct ggaccataca ttgggtggaa tgcttcttta gcaccggaag      540
cgattgggtc tttaccatat actgcgcgca gtgcgaatac ctggccagtc gggctgttca      600
ttggctgaac accacaaata tcgaagcaat caggtaggaa tagcacgccg               650
```

<210> SEQ ID NO 6
<211> LENGTH: 216
<212> TYPE: PRT
<213> ORGANISM: Unknown Organism
<220> FEATURE:
<223> OTHER INFORMATION: Description of Unknown Organism: Tail of Phage
    B3 amino acid sequence

<400> SEQUENCE: 6

```
Gly Val Leu Phe Leu Pro Asp Cys Phe Asp Ile Cys Gly Val Gln Pro
 1               5                  10                  15

Met Asn Ser Pro Thr Gly Gln Val Phe Ala Leu Arg Ala Val Tyr Gly
                20                  25                  30

Lys Asp Pro Ile Ala Ser Gly Ala Lys Glu Ala Phe His Pro Met Tyr
            35                  40                  45

Gly Pro Asp Ala Met Phe Ser Gly Gln Gly Ala Ala Lys Lys Phe Ala
        50                  55                  60

Ala Leu Lys Ala Ser Asp Thr Leu Glu Val Gly Thr Ile Tyr Thr His
    65                  70                  75                  80

Phe Phe Gln Glu Thr Gly Thr Val Tyr Leu Gln Ala Thr Glu Val Lys
                    85                  90                  95

Gln Ile Asp Ser Gly Ala Ser Asp Ala Asp Lys Leu Asp Ala Glu Ile
                100                 105                 110

Lys Lys Gln Met Glu Ala Gly Val Leu Val Glu Ile Ala Glu Gly Met
            115                 120                 125

Ala Thr Ser Ile Ala Glu Leu Gln Glu Gly Phe Asn Gly Ser Thr Asp
```

```
-continued
         130                  135                 140
Asn Pro Trp Asn Glu Met Gly Phe Arg Ile Asp Lys Gln Val Ile Glu
145                      150                 155                 160

Ala Lys Ser Arg Gln Leu Lys Ala Ala Tyr Ser Ile Glu Leu Ala Gln
                165                 170                 175

Asp Leu Arg Ala Val His Gly Met Asp Ala Asp Ala Glu Leu Ser Gly
            180                 185                 190

Ile Leu Ala Thr Glu Ile Met Leu Glu Ile Asn Arg Glu Val Val Asp
        195                 200                 205

Trp Ile Thr Thr Pro Ser Gly Gly
    210                 215
```

BACTERIOPHAGE COMPOSITION USEFUL IN TREATING FOOD PRODUCTS TO PREVENT BACTERIAL CONTAMINATION

FIELD OF THE INVENTION

The present invention is directed to a bacteriophage composition useful in treating food products to prevent bacterial contamination by *Escherichia coli* bacteria.

BACKGROUND OF THE INVENTION

The Centers for Disease Control and Prevention (CDC) estimates that as many as 33 million people develop food poisoning each year—about one out of every ten Americans—and about 9,000 die. Since many cases of food poisoning are mistaken for a 24-hour "stomach flu," the actual number of people with foodborn illness is probably much higher. Cerrato, P., "When food is the culprit; food poisoning," *RN*, 62(6):52 (Jun. 1, 1999). The presence of foodborn pathogens in a country's food supply not only affects the health of the local population, but also represents a potential for spread of pathogens to visitors to the country and to consumers in countries which import food products. Buzby et al., "Economic costs and trade impacts of microbial foodborne illness, " *World Health Stat. Q.*, 50(1–2):57–66 (1997).

Prevention of foodborne illnesses by microbial contamination is of major concern to the food processing industry, regulatory agencies, and consumers. Foodborne microbial contamination occurs both prior to entry into the processing facility, and by cross-contamination in the processing environment. The Food Safety & Inspection Service (FSIS) of the United States Department of Agriculture has instituted new Hazard Analysis and Critical Control Point (HACCP) requirements to reduce the occurrence and number of foodborne pathogens. These regulations must be met by food processors. Although the means of achieving this microbial reduction is left to the discretion of the processor, FSIS expects that antimicrobial treatments will be an important component of HACCP plans. The treatment methods of the present invention, which employ formulations of the bacteriophage compositions of the invention, are useful in meeting the HACCP requirements.

In their efforts to provide a product completely free of microbial contamination, poultry and meat processors have encountered major difficulties in removing microorganisms that infect poultry and meat tissues intended as food products.

*E. coli* Bacteria

*E. coli* bacteria are short Gram-negative rods that are part of the normal flora of the intestines of most warm-blooded animals. These organisms are the most common facultative anaerobe in the large bowel and provide protection against colonization by other harmful microbes. There are, though, five distinct groups of *E. coli* that can cause enteric disease: (1) enteroinvasive, (2) enteropathogenic, (3) enterotoxigenic, (4) enteroadherent, and (5) enterohemorrhagic. Pilot et al., "Threats from the food we eat; includes related articles; New and Emerging Pathogens, part 3," *Medical Laboratory Observer*, 28:42 (Apr. 1996).

*E. coli* 0157:H7 bacteria, first described in 1982, is a subset of the enterohemorrhagic variety that produces Shiga-like toxins (verotoxins) 1 and 2. Pilot et al. (Apr. 1996); and "Medical Experts Urge Radiation of Beef to Kill Deadly Bacteria," *The New York Times*, Jul. 14, 1994, at page A15.

The toxin produced by *E. coli* 0157:H7 in the intestines can cause anything from a mild diarrhea to severe hemorrhagic colitis, where the cells of the intestinal lining are damaged, allowing blood to pass into stool. In as many as 16% of all cases, the infection progresses to a more serious condition—hemolytic-uremic syndrome (HUS). Mackenzie, D. L., "When *E. coli* turns deadly," *RN*, 62(7):28 (Jul. 1, 1999). HUS, which occurs when the bacterial toxin enters the bloodstream through the damaged intestinal wall and travels to the smaller arteries that supply the kidneys, going on to damage those vessels, is characterized by hemolytic anemia, thrombocytopenia, and acute renal failure. In addition, anywhere from 10%–50% of patients with HUS develop long-term sequelae, including cardiomyopathy, pulmonary problems, pericardial effusions, end-stage renal disease, chronic hypertension, hyperglycemia, and encephalopathy. Mackenzie, D. L. (Jul. 1, 1999).

*E. coli* 0157:H7 is a leading cause of HUS in the United States and a leading cause of acute renal failure in children. Although the overall incidence of *E. coli* 0157:H7 infection is unknown, estimates based on a 1994 outbreak in the Seattle area suggest that more than 20,000 cases occur in this country each year, and that 250 of them result in death. Mackenzie, D. L. (Jul. 1, 1999); and "Ban the 0157:H7 Bomb," *Nutrition Action Healthletter*, 22:3 (Janurary 1995/Feburary 1995). Young children, the elderly, and people with weakened immune systems are most susceptible to infection and resulting complications.

There is no known treatment for *E. coli* 0157:H7 infection. *Nutrition Action Healthletter*, 22:3 (January 1995/Feburary 1995). Antibiotics do little to deter the infection. "Medical Experts Urge Radiation of Beef to Kill Deadly Bacteria," *The New York Times*, Jul. 14, 1994, at page A15; and Cerrato, P. (Jun. 1, 1999).

One reason this strain of *E. coli* is so dangerous is that it can cause disease in such low doses—ingestion of less than 1,000 organisms compared to more than the 10,000,000 needed before the bacterium that causes cholera causes disease. Cerrato, P. (Jun. 1, 1999). Some reports state that *E. coli* 0157:H7 can cause illness with as few as 69. *The New York Times*, Jul. 14, 1994, at page A15. As little as one-half cup of *E. coli*-contaminated cider can cause abdominal pain, bloody diarrhea, vomiting and fever. "Roadside cider may be risky; may be contaminated with *E. coli*," *Environmental Nutrition*, 16:8 (September 1993). Such small amounts of disease-causing bacteria cannot be detected by routine meat inspection practices, and the presence of contaminated food products cannot be identified by sight, taste or smell. *The New York Times*, Jul. 14, 1994, at page A15. Similarly, the pathogen's acid resistance gives it an advantage over other pathogens. Gastric acid, one of the gastrointestinal tract's first lines of defense against foodborne illness, has little effect on *E. coli* 0157:H7. Cerrato, P. (Jun. 1, 1999).

*E. coli* 0157 is found regularly in the feces of healthy cattle, and is transmitted to humans through contaminated food, water, and direct contact with infected people or animals. Mead et al., "*Escherichia coli* 0157:H7," *The Lancet*, 352(9135):1207–1212 (Oct. 10, 1998). Transmission of the infection is primarily linked to consumption of undercooked ground beef, contaminated drinking water, and unpasteurized milk. Hamburger is a major vehicle of foodborne outbreaks of *E. coli* 0157:H7 infection. Koutkia et al., "Enterohemorrhagic *Escherichia coli* 0157:H7," *American Family Physician*, 56:853 (Sep. 1, 1997).

During the slaughter process, intestinal fluid or feces of infected cattle can drip onto the surface of the meat, contaminating it. It is theorized the harmful bacteria on the surface of the raw meat become mixed throughout the meat during the grinding process, where it can better survive the heat of cooking. One hamburger patty can contain the meat from many cows.

Currently, E. coli 0157:H7 is the most common of verotoxin-producing E. coli serotypes. Various sources indicate it comprises from about 60% to more than 90% of all toxin-producing isolates and has been responsible for most outbreaks when food sources have been implicated. Pilot et al. (April. 1996). Distribution of E. coli 0157:H7 probably is worldwide; the majority of cases have been noted in North America and Europe. Pilot et al. (April 1996).

Current Methods of Treating Food Products to Eliminate Bacterial Contamination

A. Irradiation

Food irradiation is the treatment of foods by subjecting them to ionizing radiation, also called ionizing energy. The radiation used in the process comes either from radioactive isotopes of cobalt or cesium or from devices that produce controlled amounts of high-energy electrons, gamma rays, or X rays. The process does not and cannot make the food radioactive. Greenberg et al., "Irradiated Foods," *American Counsil on Sci. and Health Booklets,* 1–28 (Apr. 30, 1996).

The radiation used to treat foods is called "ionizing radiation" because it produces ions—electrically charged particles. Ionizing radiation—including X rays, gamma rays, and beams of high-energy electrons produced by electron accelerators—has a higher energy than other, nonionizing radiation such as visible light, television waves, radio waves and microwaves. Greenberg et al. (Apr. 30, 1996).

Food irradiation has been proposed as one solution to the food safety problem. Food irradiation was first approved by the FDA in 1963 for the control of insects in wheat flour and again in 1964 to prevent sprouting in potatoes. Later, it was approved for use in spices, produce, and poultry, and on Dec. 3, 1998, it was approved for beef, lamb, and pork to control disease-causing microorganisms. Klausner, A., "Food Irradiation: We May Be Zapping Up The Wrong Tree," *Environmental Nutrition,* 17(12):1 (Dec. 31, 1994).

Two radiation sources are practical for food treatment. The first is a tightly sealed metal container of radioactive elements—cobalt 60 or cesium 137—that produce gamma rays. The rays are directed onto the food being irradiated, with the food itself never being touched by the cobalt or cesium. The second type of radiation source is a machine that produces X rays and high-energy electrons. Neither of these sources has enough energy to make the irradiated foods radioactive. Greenberg et al. (Apr. 30, 1996).

During the irradiation process, food is carried on a conveyor belt into a sealed chamber where it is hit with large doses of energy from a radiation source (usually gamma rays from radio-active cobalt). The energy disrupts molecules in the food, killing insects, molds, fungi and bacteria that cause spoilage, as well as pathogens that cause foodborne illnesses. Klausner, A. (Dec. 31, 1994).

Consumer advocates warn that food irradiation is not a panacea. In fact, they say, it poses safety risks of its own. For example, food irradiation opponents cite research showing the process depletes nutrients (vitamins A, C, and the B vitamin, thiamin). The greater the radiation dose, the greater the losses. In addition, an irradiated food must still undergo normal nutrient-depleting processing, compounding the losses. Klausner, A. (Dec. 31, 1994).

Food irradiation also forms residual substances such as benzene and formaldehyde—both known carcinogens. And it produces free radicals and chemically altered food components called radiolytic products, whose long-term health effects are unknown. Klausner, A. (Dec. 31, 1994). It is hypothesized that changes from such food irradiation could lead to more cancers. Id. Moreover, reports on consumer acceptance are mixed. Taste tests for irradiated beef first reported in *The Economist* failed miserably, as consumers described a "burnt-hair" taste. Klausner, A. (Dec. 31, 1994).

Another drawback of irradiation as an bacterial-control process is that irradiation, like heat treatment, does not leave any active agent in an unpackaged food to protect it against reinfestation. Greenberg et al. (Apr. 30, 1996).

B. Chemical Treatments of Meat

Several chemical and physical methods have been proposed to reduce microorganisms in meat products, such as the use of chlorine or chlorine dioxide, ozone, hydrogen peroxide, lactic acid, sodium carbonate, trisodium phosphate, and electrical stimulation. Generally, these methods have shown limited effectiveness in reducing microbial contamination and may affect the physical appearance of the meat products. In addition, such studies show that frequently unacceptably high levels of chemicals are required to kill pathogens such as E. coli 0157:H7. Id.

For example, U.S. Pat. No. 5,366,983, incorporated herein by reference, discloses a method for removing or preventing Salmonella contamination of meat products by treatment with an effective amount of an aqueous solution of a quaternary ammonium cationic surfactant, such as alkylpyridinium, particularly cetylpyridinium chloride (CPC) and cetylpyridinium bromide (CPB).

Disinfestation by irradiation can substitute for some of the former uses of the now-banned fumigant ethylene dibromide (EDB). The possibility of such a replacement is one of the major reasons for renewed interest in irradiation in the United States, as the chemical fumigants being used currently in place of EDB have serious disadvantages, including increased hazards for the workers who must apply them. Greenberg et al. (Apr. 30, 1996).

Another disadvantage of chemical disinfectants is that residues of such chemicals invariably remain on the foodstuffs. Greenberg et al. (Apr. 30, 1996).

Treatment with chemical disinfectants can also produce resistant bacteria. "Growing Menace: Antibiotic-Resistant 'Supergerms'," *The Int'l. Council for Health Freedom Newsletter,* II(3–4):18 (Fall, 1998); Freeman, C., "Antimicrobial Resistance: Implications for the Clinician," *Critical Care Nursing Q.,* 20(3):21 (Nov. 1997).

C. Pulsed Light

Yet another method for treating food products to eliminate bacterial contamination is treatment with high intensity light emissions, produced by a pulsed power energization technique (PPET). MacGregor et al., "Light inactivation of food-related pathogenic bacteria using a pulsed power source," *Letters in Applied Microbiology,* 27(2):67–70 (1998). This process comprises dissipating many megawatts (MW) of peak electrical power in the light source in an extremely short energization time (about 1 (mu)s). The light source is subjected to electric field levels greater than could be achieved under conventional continuous operation, which leads to a greater production of the shorter bacteriocidal wavelengths of light.

The usefulness of this process is limited, as the pulsed light emissions can only significantly reduce bacterial populations on exposed surfaces. Such a process is not useful for treating, for example, ground hamburger. This is significant as recent studies indicate that E. coli bacteria can be present on the interior of foodstuffs such as apples, which would not be treatable using a pulsed light process. Buchanan et al., "Contamination of intact apples after immersion in an aqueous environment containing *Escherichia coli* 0157:H7," *J Food Prot.,* 62(5):444–50 (May, 1999).

There is a need in the art for a superior composition and method for treating food stuffs to eliminate bacterial contamination by E. coli bacteria, particularly toxin-producing E. coli bacteria. The present invention satisfies these needs.

SUMMARY OF THE INVENTION

The present invention is directed to novel phage compositions useful in treating food products to minimize or eliminate bacterial contamination by E. coli bacteria, particularly toxin-producing E. coli bacteria. The phage compositions can be formulated with suitable carriers.

Also encompassed by the invention are methods of treating food products, it such as meat (including but not limited to poultry, beef, lamb, and pork), juices, spices, and produce.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 1: Provides a description of the open reading frames (ORFs) of Phage 119U;

FIG. 2: Shows the DNA sequence of the head of Phage B1 (SEQ ID NO. 1);

FIG. 3: Shows the DNA sequence of the tail of Phage B1 (SEQ ID NO. 2);

FIG. 4: Shows the amino acid sequence of the tail of Phage B1 (SEQ ID NO. 3);

FIG. 5: Shows the DNA sequence of the head of Phage B3 (SEQ ID NO. 4);

FIG. 6: Shows the DNA sequence of the tail of Phage B3 (SEQ ID NO. 5);

FIG. 7: Shows the amino acid sequence of the tail of Phage B3 (SEQ ID NO. 6);

FIG. 8: Shows the host ranges for the bacteriophages B1, B3, 146A, and 119U against a large number of E. coli isolates;

FIG. 9: Shows the growth of bacteria over time as compared to the concentration of Phage 119U;

FIG. 10: Shows the growth of bacteria over time as compared to the concentration of Phage B3; and FIG. 11: Shows the host range of Phages B1 and B3 against thirty-three different strains, and fifteen different serotypes, of human and porcine E. coli, including the toxin producing E. coli strain 0157.

DETAILED DESCRIPTION OF THE PREFERRED EMBODIMENTS

The present invention is directed to novel phage compositions useful in treating food products to minimize or eliminate bacterial contamination by E. coli bacteria, particularly toxin-producing E. coli bacteria. The phage compositions can be formulated with suitable carriers.

Bacteriophages B1 and B3 were isolated from raw sewage using an E. coli 0157:H7 strain as a host. Phages 146A and 119U were isolated against a urinary tract infection (UTI) isolate. Phages B1 and B3 were deposited at the American Type Culture Collection (Manassas, Va.) under Accession Nos. 203000 and 209999 on Jun. 24, 1998. Phage 146A was deposited under Accession No. 55950 on April 14, 1997, and Phage 119U was deposited under Accession No. 209998 on Jun. 24, 1998, both at the American Type Culture Collection. The bacteriophage compositions can be in an aqueous or non-aqueous medium.

The present invention provides a method for preventing growth of microorganisms on food products comprising contacting a food product with a microbial growth inhibiting effective amount of a bacteriophage composition comprising the bacteriophage isolate B1, B3, 119U, 146A, or a combination thereof, for the prevention of growth of E. coli microorganisms on food products. The prevention of growth of microorganisms on food products is intended to provide a food product that is devoid of or contains minimal numbers of viable microorganisms that could cause illness in humans or animals or spoilage of the food product prior to ingestion.

The prevention of growth of microorganisms on food products is intended to include but is not limited to the following mechanisms: (1) removal of attached microorganisms from the food products; (2) inhibition of attachment of microorganisms to the food products; (3) killing or inactivation of attached microorganisms on the food products; and (4) killing or inactivation of microorganisms which are not attached to the food product but which are present in liquids associated with the food products during processing; such as in chill tanks, or which are present on surfaces associated with food preparation, liquids remaining on such surfaces, such as countertops, cutting boards and sinks, and equipment used in food preparation and sanitization of the food.

The present invention has an important application in the food processing industry, as well as for home and institutional food preparation. The bacteriophage compositions of the invention are readily available and the cost of carrying out the method of the present invention is not expensive as compared to existing antimicrobial processes. Unlike existing treatments using, for example, trisodium phosphate, the use of the bacteriophage compositions of the invention does not alter the appearance, color, taste, or texture of the food product. Moreover, the bacteriophage compositions of the invention are non-toxic.

The bacteriophage composition is applied for a period of time sufficient to kill E. coli bacteria present on the food product. It is important that the application time of the bacteriophage compositions is for a sufficient time to result in significant prevention of growth of E. coli microorganisms on the food product.

The present invention also includes methods of contacting the bacteriophage compositions of the invention with food products, including but not limited to, spraying or misting the compound on the food product, or by immersing the food product in a composition comprising one or more bacteriophages of the invention.

The present invention is intended to encompass any method that contacts the bacteriophage compositions of the invention with a food product by any direct means, including spraying, misting, dipping, or soaking. But the present invention also is intended to include contact of the bacteriophage compositions of the invention with the food by indirect means, such as applying the bacteriophage compositions of the invention to equipment or food product processing or preparation surfaces in which the food product is contacted during processing, preparation, storage, and/or packaging.

Any type of method of contact of the bacteriophage compositions with the food product is useful in the present method as long as it is capable of allowing a short application time. A method that utilizes a cabinet that provides spraying or misting of the food product is useful in the present invention. Machinery for use in such cabinets on a processing line in a food processing plant are adaptable for reducing the application time to a minimum while still obtaining efficacious antimicrobial effects on the food.

The present method is useful, for example, in a poultry processing plant for treating post-chilled chickens that have been immersed in a chill bath of cold water. The chickens are removed from the chill bath and treated with the bacteriophage compositions of the invention for an application time sufficient to result in significant prevention of growth of microorganisms on the chickens. The treated chickens are subsequently packaged without further washing or rinsing. However, the method optionally may include, if deemed necessary, at least one washing step of the chickens prior to packaging. The optional washing step may include spraying or misting the food product with water or immersing the food product in a container or tank of water.

Further, the method of the present invention can optionally include a determination step prior to contacting the food product with the bacteriophage compositions of the invention to determine the presence of microorganisms on the food before treatment.

Any conventional methods for rapidly determining the presence of microorganisms can be utilized as the determination step, which for example, includes PCR and immunoassays.

Additionally, the method of the present invention optionally includes a step to determine the presence of the bacteriophage compositions of the invention on the surface of the food product after contact with the bacteriophage compositions. This determination is performed immediately after the contacting step or after several washing steps. For example, the bacteriophage compositions of the invention is extracted from the tissues of the food in a form suitable for high performance liquid chromatography (HPLC) analysis.

The food processing industry, as well as home, restaurant or institutional food preparation, is in need of more effective products and processes for the prevention of growth of a broad range of contaminating microorganisms on many different food products and/or surfaces that the food products and juices or liquids from the food come in contact. This is especially true for microorganisms which are attached to the surfaces of food. As a result of increasing numbers of illnesses caused by foodborne pathogenic microorganisms, the food processing industry now requires more effective processes for the removal and prevention of a broader spectrum of microorganisms, and particularly for pathogenic microorganisms, such as, toxin-producing *Escherichia coli*, such as *E. coli* 01 57:H7, which are known to cause serious human diseases as a result of food contamination. The present invention provides a composition comprising at least one bacteriophage of the invention and methods of preventing the growth of microorganisms on and in the food, as well as in liquids and on surfaces associated with food products and their preparation. This method of prevention is an important goal in preventing cross-contamination from infected food products; in removing attached microorganisms from food products; in inhibiting the attachment of microorganisms to the food products; and in preventing the growth of microorganisms that remain attached to the food products. Further, the method of the present invention can easily be adapted for use in a food processing plant.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to describe the isolation and characterization of the novel bacteriophages B1, B3, and 119U.

Bacteriophages B1, B3, and 119U were isolated from raw sewage using an *E. coli* 0157:H7 strain as a host. The strains were isolated according to the method described in U.S. Pat. No. 6,121,036, which is specifically incorporated by reference.

The method comprised (a) obtaining a sample containing a bacteriophage to at least one bacterial organism selected from the group consisting of staphylococci, hemophilia, helicobacter, mycobacterium, mycoplasmi, streptococci, neisserii, klebsiella, enterobacter, proteus, bacteriodes, pseudomonas, borrelii, citrobacter, escherichia, salmonella, propionibacterium, treponema, shigella, enterococci and leptospirex; (b) dispersing the sample in phosphate buffered saline; (c) filtering the dispersed sample through a filter that will retain the bacterial organism and allow the bacteriophage to pass; (d) purifying the bacteriophage that passes through the filter; (e) growing bacteriophage in medium containing at least one of the bacterial organisms; (f) selecting and isolating bacteriophage preparations achieving titers higher than about $10^8$ to $10^9$ bacteriophages per plaque after about eight hours to provide an isolated bacteriophage; (g) purifying the isolated bacteriophage; and (h) repeating steps (e)–(g) at least 5 times using the purified isolated bacteriophage of step (g) in step (e) to prepare the bacteriophage preparation.

All phage isolates were plaque purified at least 3 times to obtain a pure culture. Large scale preparations were done using CsCl equilibrium gradient centrifugation. (Gilakjan et al., *J. Bacteriol.*, 181:7221–7 (1999)).

There are six major families of bacteriophages, one of which is Myoviridae, also known as T-even bacteriophages. (U.S. Pat. No. 6,090,541.) Phages B1 and B3 are similar in morphology to the T-even phages (i.e., T2, T4, and T6), which includes the well characterized T4.

Phage 119U is unique in its genome (sequence), host range, and virulence; it has both strain K1 and K5 antigen lysase genes; and it is non-toxic and efficacious. Phage 119U, having a linear double-strand DNA genome of 44 kb is highly effective against the highly virulent K1 and K5 strains of *E. coli*, as its sequence codes for both the K1- and K5-specific proteins. FIG. 1 provides a description of the open reading frames (ORFs) of Phage 119U. Phage 119U shows no evidence of lysogeny, horizontal gene transfer, virulence genes (conferring virulence to a bacterial host), or toxin genes (conferring toxicity to a bacterial host).

EXAMPLE 2

The purpose of this example was to isolate and characterize bacteriophage 146A.

Phage 146A was isolated against a urinary tract infection (UTI) isolate using the method described in Example 1.

Phage 146A is also similar to the T-even phages but appears to have a slightly smaller head structure than the others. (Aebi et al., "Comparison of the Structural and Chemical Composition of Giant T-even Phage Heads," *J. Supramol. Struct.*, 5(4):475–495 (1977); Russell, R. L., "Comparative Genetics of the T Even Bacteriophages,"

Genetics, 78(4):967–988 (1978); and Kutter et al., "Evolution of Tr-related Phages," Virus Genes, 11(2–3):285–297 (1995)).

EXAMPLE 3

The purpose of this example was to prepare restriction digests and partial sequences for the bacteriophages B1 and B3 to further characterize the phages.

Restriction Digests

DNA preparations for B1 and B3 were made from CsCl stocks using the phenol/chloroform extraction method. (Chomczynski et al., Analyt. Biochem., 162:156–159 (1987)).

Restriction digests Phages B1 and B3 were performed. Digested DNA was run on 0.6–0.7% TAE (Tris-acetate-ethylenediamine tetraacetic acid (EDTA)] running buffer agarose gels with a λ HinDIII marker. The restriction enzymes EcoRI, BamHI, HinDIII, PstI, XhoI, and BglI all failed to cut either B1 or B3 DNA. The only two enzymes that did cut were DraI and VspI.

These results are typical of the T-even phages; the DNA of T-even phages contains D-glucosyl hydroxymethyl cytidine instead of cytidine, which blocks cleavage by most restriction enzymes. DraI and VspI are able to cut because there are no G-C base pairs in their recognition sequences. The restriction patterns for DraI and VspI digests of B1, B3, and T4 are all different.

Phages B1 and B2 were restriction mapped, with the resulting maps being unique as compared to all other published DNA enzyme restriction maps.

Partial Sequencing

The DNA sequence of the head and tail of Phage B1 is shown in FIGS. 2 and 3, respectively, and the amino acid sequence of the tail of Phage B1 is shown in FIG. 4. In addition, the DNA sequence of the head and tail of Phage B3 is shown in FIGS. 5 and 6, respectively, and the amino acid sequence of the tail of Phage B3 is shown in FIG. 7. Phages B1 and B3 are estimated to have genomes of about 150,000 bp.

EXAMPLE 4

The purpose of this example was to determine the host ranges for the acteriophages B1, B3, 146A, and 119U against a large number of urinary tract infection (UTI) E. coli isolates. Bacteriophage 119U is specific to E. coli strain K1, and probably E. coli strain K5.

Host Ranges of B1, B3, 146A, and 119U $10^4$ pfu of each phage was spotted on a lawn for each UTI bacterial isolate and the plate was incubated overnight at 37° C. A plus (+) indicates complete clearing, a plus(t) (+(t)) indicates a turbid spot, a plus(p) (+(p)) indicates a spot that has small individual plaques, and a minus (−) indicates that the phage had no effect on the bacterial isolate.

All four phages showed fairly broad host ranges. Individually, the host range of the four phage preparations was 30 to 60%, and collectively the host range was 84%. Each isolate lysed at least 40% of the E. coli isolates, as shown in FIG. 8. In addition, the phages complement each other as they overlap in their ability to clear the bacterial isolates.

Specifically, Phages B1 and B3 lysed 57% and 49%, respectively, of the 61 E. coli UTI isolates, and additionally lysed E. coli strain K12; and Phages 146A and 119U lysed 31% and 30%, respectively, of the 61 E. coli UTI isolates. See FIG. 8.

Phage T4 did not lyse any of the UTI isolates, as it only grew on E. coli K12 (ATCC Deposit No. 29425) (data not shown).

EXAMPLE 5

The purpose of this example was to analyze the efficacy of phages 119U and B3 by determining the minimal amount of phage that will lyse a susceptible bacteria grown in urine.

The urine used was collected from a healthy adult male, and was sterilized by passing through a 0.45 µM filter. 50 ml flasks of urine were inoculated with 100 µl of an LB overnight culture of E. coli 119U. The innoculum was spun down and washed in urine to remove any residual LB media. $10^2$, $10^4$, and $10^6$ pfu of Phage 119U or B3 was added at the beginning, one flask had zero phage. The cultures were incubated at 37° C. with moderate shaking (200 rpm in New Brunswick incubator). OD 600 was measured to monitor bacterial growth.

The results showed that as little as $10^2$ pfu of Phage 119U completely lysed the culture. See FIG. 9 (Phage 119U) and 10 (Phage B3), showing the growth of bacteria over time as compared to the concentration of phage. With no phage, bacterial growth (correlated to absorbance) dramatically increased, whereas with the presence of phage, bacterial growth rapidly declined to approximately 0.

EXAMPLE 6

The purpose of this example was to determine the toxicity of Phages 119U and B1.

No acute toxicity was observed following injecting a large dose of Phage 119U in mice (up to $10^6$ times of efficacy level), while Phage B1 showed no toxicity in animals.

To test for toxicity of Phages 119U and B1, aliquots of each phage of $3.4 \times 10^{11}$ pfu/ml (Phage 119U) and $3.2 \times 10^{12}$ pfu/ml (Phage B1) were prepared for acute toxicity studies by diluting samples in PBS to produce final titers of $10^{10}$ and $10^6$ pfu/ml. The Limulus amebocyte lysate (LAL) test was performed on the $10^{10}$ pfu/ml stock of each phage. The endotoxin levels for the samples of Phage B1 and 119U were determined to be ~6 EU/ml and <6 EU/ml, respectively.

The acute toxicity study was conducted using 30 CD-1 female mice (19–21 g). The mice were divided into six groups of five, and treated as follows:

Group 1: no injection

Group 2: intraperitoneal injection with 100 µl sterile saline

Group 3: intraperitoneal injection with 100 µl phage B1 ($10^9$ pfu)

Group 4: intraperitoneal injection with 100 µl phage B1 ($10^5$ pfu)

Group 5: intraperitoneal injection with 100 µl phage 119U ($10^9$ pfu)

Group 6: intraperitoneal injection with 100 µl phage 119U ($10^5$ pfu)

Mice were monitored (visual observation, random temperatures) over the three days following the injections. All mice in the experimental groups appeared active and healthy, identical to the control groups. This demonstrates that phage obtained according to the claimed invention are non-toxic.

EXAMPLE 7

The purpose of this example was to determine the host range of Phages B1 and B3 against thirty-three different strains, and fifteen different serotypes, of human and porcine E. coli, including the toxin producing E. coli strain 0157. The strains were obtained from a research collection.

$10^4$ pfu of each phage was spotted on a lawn for each bacterial isolate and the plate was incubated overnight at 37°

C. A plus (+) indicates complete clearing, a minus (−) indicates that the phage had no effect on the bacterial isolate, and a plus/minus (+/−) indicates that the bacteriophage had partial efficacy against the *E. coli* isolate.

Both Phage B1 and B3 showed broad host ranges, including against the toxin-producing *E. coli* 0157 strains. See FIG. 11. Phage B1 lysed or had activity against 26 of the 33 strains (79%), and lysed or had activity against 10 of the 15 serotypes of *E. coli* (67%). Phage B3 lysed or had activity against 27 of the 33 strains (82%), and lysed or had activity against 11 of the 15 serotypes of *E. coli* (73%).

These results demonstrate the usefulness of the bacteriophage compositions of the invention for preventing or treating contamination of food products by toxic and non-toxic *E. coli* strains.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A purified bacteriophage composition comprising the bacteriophage isolate B1.

2. A purified bacteriophage composition comprising the bacteriophage isolate B3.

3. A purified bacteriophage composition comprising the bacteriophage isolate 119U.

4. A purified bacteriophage composition comprising the bacteriophage isolate 146A.

5. A bacteriophage composition comprising at least two bacteriophage isolates selected from the group consisting of B1, B3, 119U, and 146A.

6. A method for preventing the growth of *E. coli* microorganisms on a food product comprising:
    contacting said food product with a microbial growth inhibiting effective amount of a bacteriophage composition comprising the bacteriophage isolate B1, wherein the application time of said bacteriophage composition is for at least a fraction of a second to prevent the growth of microorganisms on the food product.

7. The method of claim 6, wherein said contact is by spraying, misting, dipping, or soaking.

8. The method of claim 6, additionally comprising a washing step in which the food product is contacted with an aqueous medium to remove the bacteriophage composition.

9. The method of claim 6, wherein the food product is selected from the group consisting of fruit juices, vegetable juices, produce, poultry, beef, lamb, and pork.

10. The method of claim 6, wherein the *E. coli* microorganism is a toxin-producing *E. coli* strain O157.

11. A method for preventing the growth of *E. coli* microorganisms on a food product comprising:
    contacting said food product with a microbial growth inhibiting effective amount of a bacteriophage composition comprising the bacteriophage isolate B3, wherein the application time of said bacteriophage composition is for at least a fraction of a second to prevent the growth of microorganisms on the food product.

12. The method of claim 11, wherein said contact is by spraying, misting, dipping, or soaking.

13. The method of claim 11, additionally comprising a washing step in which the food product is contacted with an aqueous medium to remove the bacteriophage composition.

14. The method of claim 11, wherein the food product is selected from the group consisting of fruit juices, vegetable juices, produce, poultry, beef, lamb, and pork.

15. The method of claim 11, wherein the *E. coli* microorganism is a toxin-producing *E. coil* strain O157.

16. A method for preventing the growth of *E. coli* microorganisms on a food product comprising:
    contacting said food product with a microbial growth inhibiting effective amount of a bacteriophage composition comprising the bacteriophage isolate 119U, wherein the application time of said bacteriophage composition is for at least a fraction of a second to prevent the growth of microorganisms on the food product.

17. The method of claim 16, wherein said contact is by spraying, misting, dipping, or soaking.

18. The method of claim 16, additionally comprising a washing step in which the food product is contacted with an aqueous medium to remove the bacteriophage compositions.

19. The method of claim 16, wherein the food product is selected from the group consisting of fruit juices, vegetable juices, produce, poultry, beef, lamb, and pork.

20. The method of claim 16, wherein the *E. coli* microorganism is a toxin-producing *E. coli* strain O157.

21. A method for preventing the growth of *E. coli* microorganisms on a food product comprising:
    contacting said food product with a microbial growth inhibiting effective amount of a bacteriophage composition comprising the bacteriophage isolate 146A, wherein the application time of said bacteriophage composition is for at least a fraction of a second to prevent the growth of microorganisms on the food product.

22. The method of claim 21, wherein said contact is by spraying, misting, dipping, or soaking.

23. The method of claim 21, additionally comprising a washing step in which the food product is contacted with an aqueous medium to remove the bacteriophage composition.

24. The method of claim 21, wherein the food product is selected from the group consisting of fruit juices, vegetable juices, produce, poultry, beef, lamb, and pork.

25. The method of claim 21, wherein the *E. coli* microorganism is a toxin-producing *E. coli* strain O157.

26. A method for preventing the growth of *E. coli* microorganisms on a food product comprising:
    contacting said food product with a microbial growth inhibiting effective amount of a bacteriophage composition comprising at least two bacteriophage isolates selected from the group consisting of B1, B3, 119U, and 146A, wherein the application time of said bacteriophage composition is for at least a fraction of a second to prevent the growth of microorganisms on the food product.

27. The method of claim 26, wherein said contact is by spraying, misting, dipping, or soaking.

28. The method of claim 26, additionally comprising a washing step in which the food product is contacted with an aqueous medium to remove the bacteriophage composition.

29. The method of claim 26, wherein the food product is selected from the group consisting of fruit juices, vegetable juices, produce, poultry, beef, lamb, and pork.

30. The method of claim 26, wherein the *E. coli* microorganism is a toxin-producing *E. coli* strain O157.

31. A method for preventing the growth of *E. coli* microorganisms on a surface which comes in contact with food comprising:

contacting said surface with a microbial growth inhibiting effective amount of a bacteriophage composition comprising at least two bacteriophage isolates selected from the group consisting of B1, B3, 119U, and 146A, wherein the application time of said bacteriophage composition is for at least a fraction of a second to prevent the growth of microorganisms on the food product.

32. The method of claim 31, wherein said contact is by spraying, misting, dipping, or soaking.

33. The method of claim 31, wherein the surface comes in contact with one or more food products selected from the group consisting of fruit juices, vegetable juices, produce, poultry, beef, lamb, and pork.

* * * * *